United States Patent [19]

Leduc

[11] Patent Number: 5,364,602
[45] Date of Patent: Nov. 15, 1994

[54] STERILIZATION SYSTEM

[76] Inventor: Steven Leduc, 10807 E. Harvard Dr., Aurora, Colo. 80014

[21] Appl. No.: 104,981

[22] Filed: Aug. 10, 1993

[51] Int. Cl.⁵ ............................................. B01J 3/04
[52] U.S. Cl. .................... 422/307; 422/295; 34/195
[58] Field of Search ............... 34/195, 196, 197, 198, 34/199, 15; 422/26, 242, 307, 1, 295, 298, 299, 305

[56] References Cited

U.S. PATENT DOCUMENTS

| | | | |
|---|---|---|---|
| 4,461,097 | 7/1984 | Thornton | 422/295 X |
| 4,476,590 | 10/1984 | Scales et al. | 128/92 C X |
| 4,592,896 | 6/1986 | Runnells et al. | 422/295 X |
| 4,650,646 | 3/1987 | Cummings et al. | 422/26 |
| 4,671,943 | 6/1987 | Wahlquist | 422/300 |
| 4,710,350 | 12/1987 | Peterson | 422/37 |
| 4,869,872 | 9/1989 | Baltes | 422/1 |
| 4,894,207 | 1/1990 | Archer et al. | 422/292 |
| 4,909,999 | 3/1990 | Cummings et al. | 422/298 |
| 4,974,663 | 12/1990 | Nakaji | 422/295 X |
| 5,087,419 | 2/1992 | Lutz | 422/33 X |
| 5,120,512 | 6/1992 | Masuda | 422/297 |
| 5,132,084 | 7/1992 | Harrell et al. | 422/26 |

Primary Examiner—Robert J. Warden
Assistant Examiner—E. Leigh Dawson
Attorney, Agent, or Firm—Ryan, Kees & Hohenfeldt

[57] ABSTRACT

A sterilization system attachable to an autoclave or in the form of a free-standing auxiliary unit adapted to receive cassette sterilization containers for causing a high volume of air heated to an effective drying temperature to flow into said chamber at a high air flow rate. A control effective to open a valve when the unit for supplying heated air is operating and to close the valve when the unit is not operating. A device for supporting medical or dental instruments during sterilization is also disclosed.

4 Claims, 3 Drawing Sheets

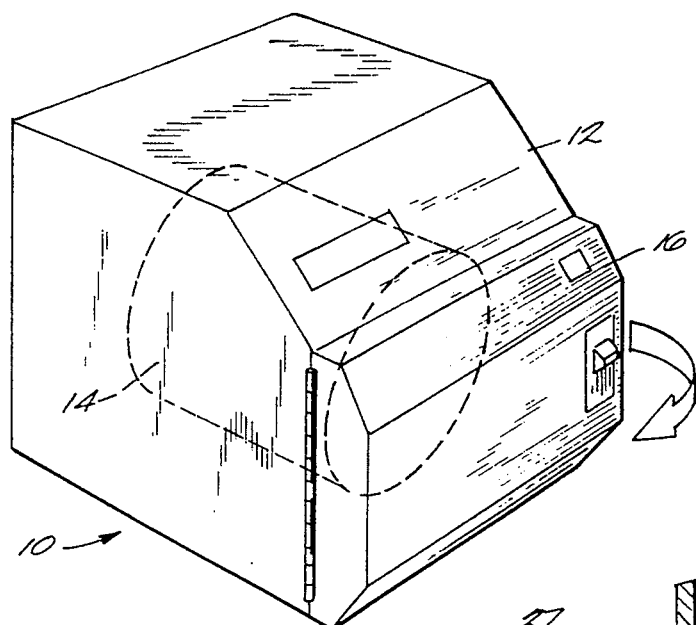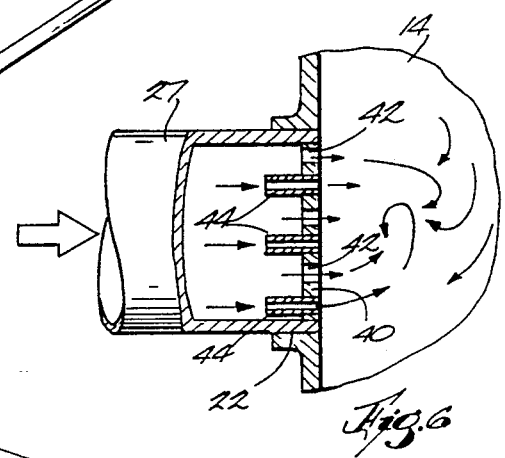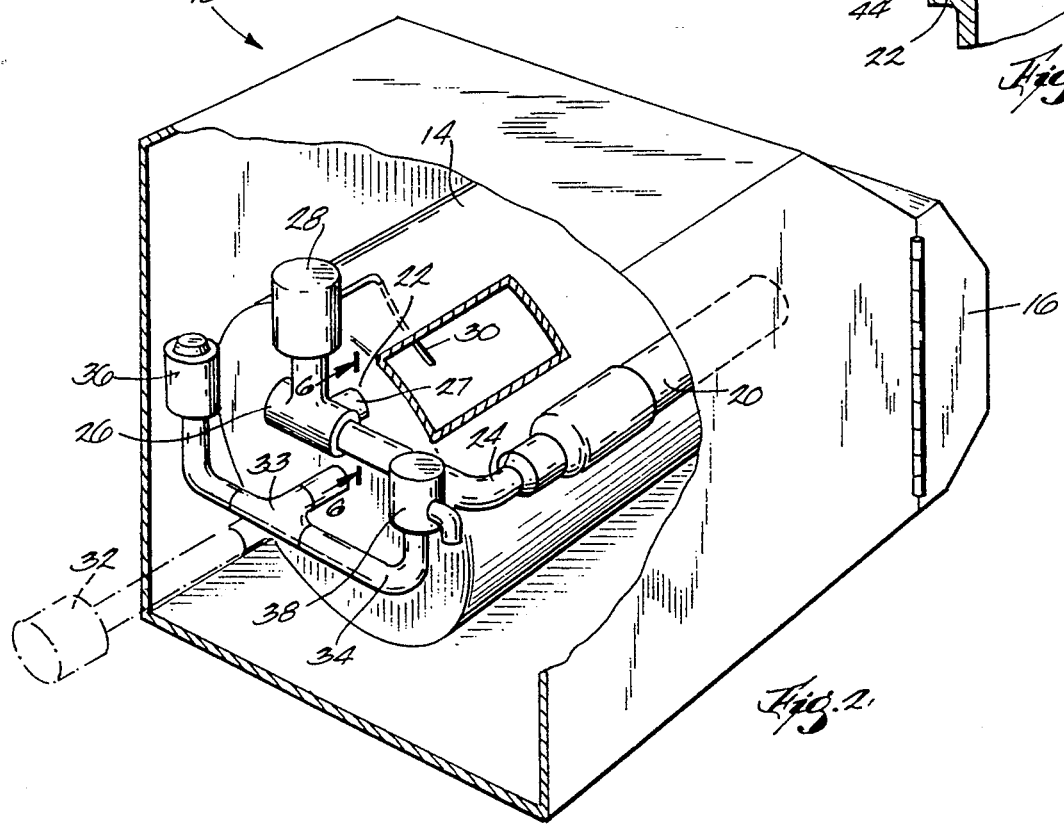

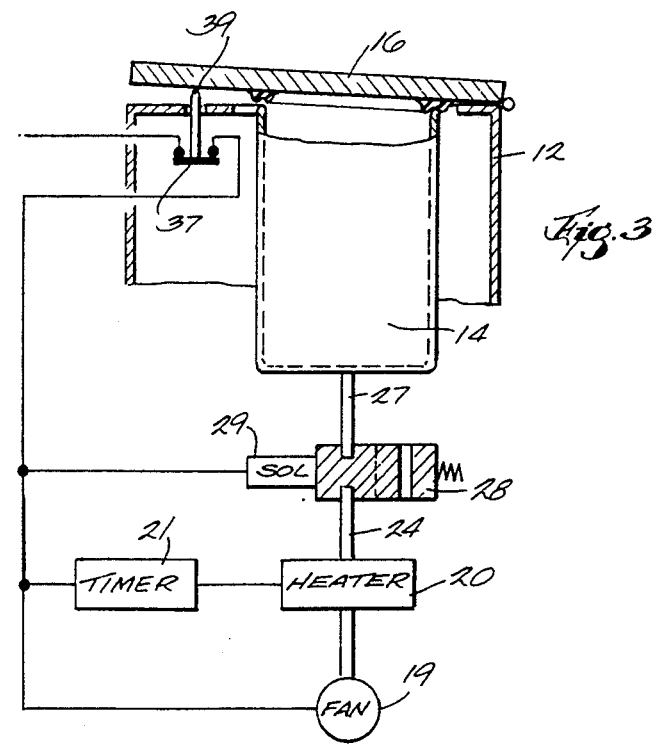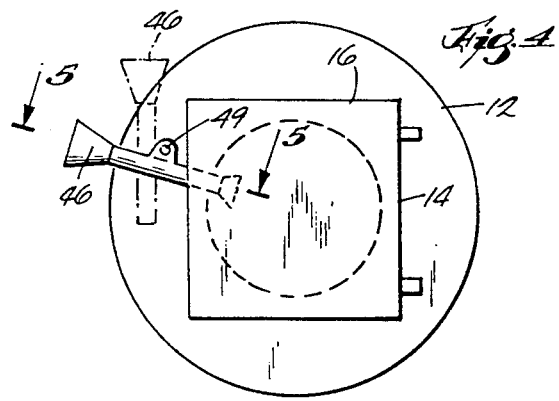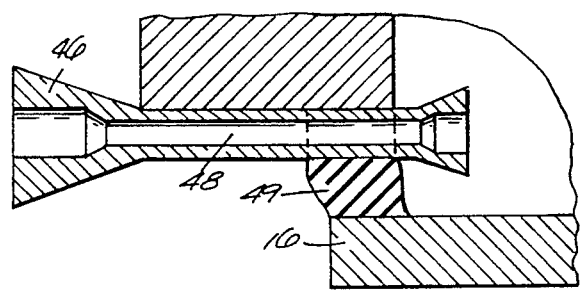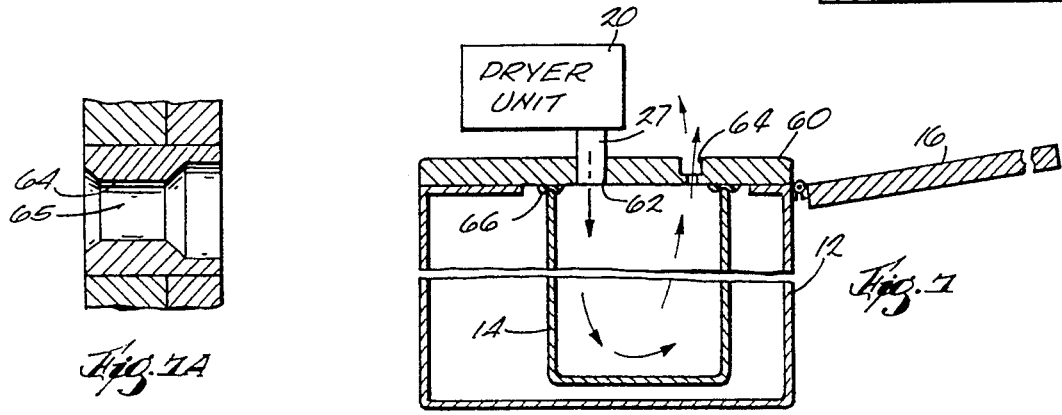

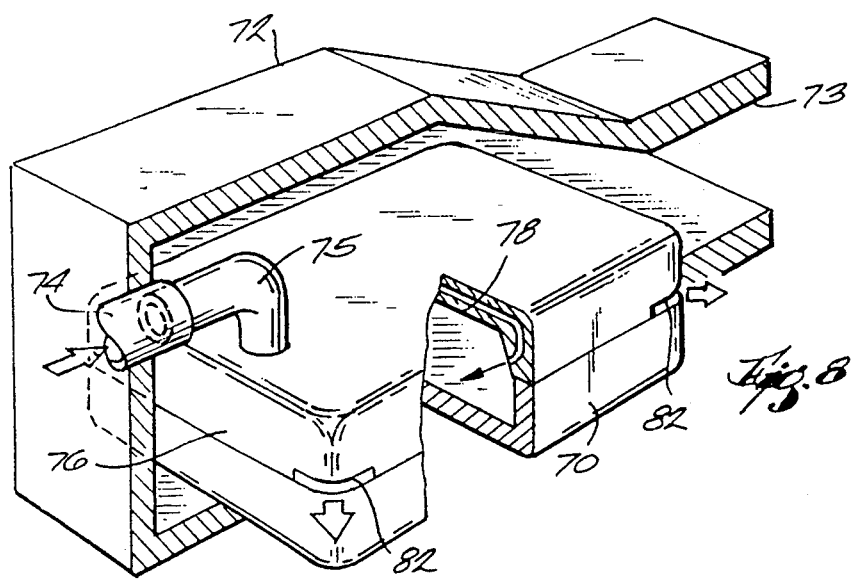
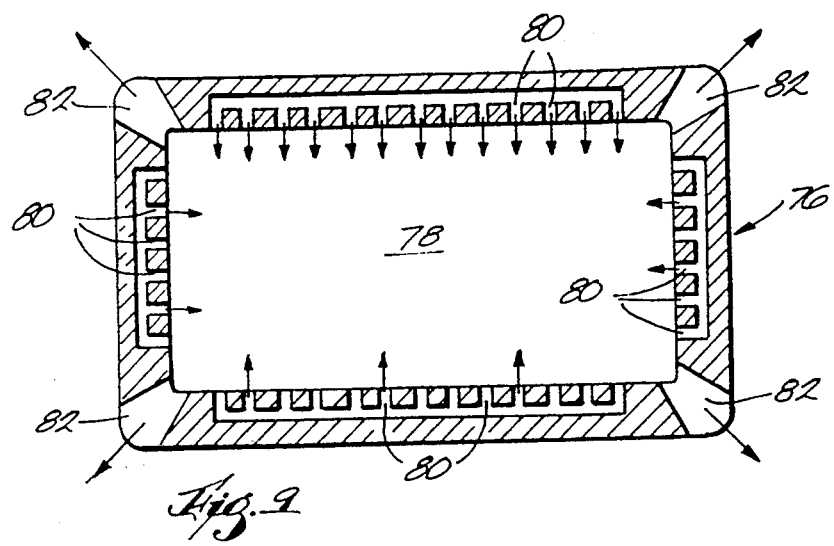
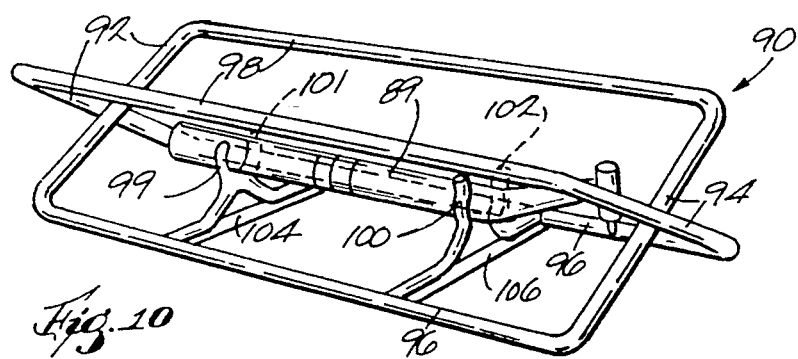

STERILIZATION SYSTEM

FIELD OF THE INVENTION

This invention relates to sterilization equipment. More specifically, the invention relates to systems capable of providing hot air drying in combination with conventional steam sterilization procedures.

BACKGROUND OF THE INVENTION

Medical and dental instruments are typically sterilized by treatment by moist heat or steam in a pressurized autoclave. In spite of the sterilization that is achieved, it has been found that microorganisms, such as the aids virus, H.I.V., and hepatitis can within tiny droplets of moisture that are typically present after autoclaving, infect the sterilized instruments once exposed to the atmosphere. Often instruments are placed in a paper and/or plastic bag for sterilization. Such bags, however, if still moist after autoclaving permit reinfection of the instruments either by air-borne or hand transferred bacteria which can penetrate the walls of the moist bags. Thus a significant need exists for improved systems for maintaining the sterility of such instruments after autoclaving.

SUMMARY OF THE INVENTION

The present invention proposes to overcome this problem by means of a follow-up hot air drying system to eliminate the tiny water droplets. The system can be retrofitted as an attachment to existing autoclave equipment or built into new equipment.

In accordance with an aspect of the invention the device includes conduits for piping heated air into the autoclave from a very high volume, high temperature air heater/blower. The air either is allowed to escape by opening the cover to the autoclave slightly or by providing a separate outlet conduit. In accordance with a further aspect the inlet is provided with a solenoid-controlled valve that prevents the escape or back-up into the heater of steam from the autoclave during the autoclave cycle. In accordance with a related aspect, a control system operates the solenoid and the heater to a preselected cycle. Optionally, a second cool (ambient temperature) air cycle can be included for the purpose of cooling down the sterilized instruments so that they can be safely handled.

Briefly summarized, the invention provides a follow-up to the sterilization cycle that utilizes the closed chamber for subjecting materials to be sterilized to a pressurized moist atmosphere at an elevated temperature and the chamber is connected to an auxiliary unit that allows a high volume of air heated to a temperature that causes the instruments to be dried without causing temperature damage to the instruments. The invention thus preserves the integrity of the sterilization process by eliminating moisture in and on the instruments. A fluid flow conduit connects the auxiliary unit to an inlet into the enclosed chamber. A fluid flow control valve in the conduit prevents flow of pressurized atmosphere from the enclosed chamber into the auxiliary unit when the auxiliary unit is not operating. A control is provided effective to open the valve when the auxiliary unit is operating and to close the valve when the auxiliary unit is not operating.

In accordance with further aspects of the invention, the chamber is provided with an access door that is normally closed during an operation of the chamber and which further includes means to disable the auxiliary unit when the door is closed. In accordance with a yet further aspect of the invention, the means to disable the auxiliary unit is in the form of an extendable and retractable stop that is extended to operate a switch to allow operation of the unit when the door is open and when the stop is retracted the auxiliary unit is prevented from operating. In accordance with a further embodiment, a vacuum pump can be connected to the fluid flow conduit between the chamber and the valve in order to assist in removal of moisture from the system. In accordance with a still further embodiment of the invention, a venturi outlet opening is provided on the chamber at a location spaced from the inlet conduit connection. The venturi alters air flow patterns within the chamber and assists in drawing the moisture contained in the system toward and out through the venturi outlet.

A still further embodiment of the invention contemplates the use of an enclosed cassette in the form of a tray and cover within which the materials to be sterilized are subjected to pressurized moist atmosphere at an elevated temperature. The sterilization cover is removable and a second cover is provided to permit flow of heated air into the cassette by insertion of the same into an auxiliary unit for causing a high volume of heated air into the cassette. The second cover has an air flow inlet intermitting with an air flow supply conduit in the auxiliary unit. Preferably, the air flow inlets supply conduits are each provided with intermitting connect couplings. Preferably, outflow openings are provided either at each corner of the tray or through the top or sides thereof. The second cover may include a baffle spaced from the top of the tray for directing flow of air from an inlet connected to the top toward the sides of the tray to provide for uniform distribution of heated air throughout the tray.

In accordance with an alternate embodiment of the invention, a separate door panel is provided for the purpose of providing inflow openings into an autoclave chamber for input of heated air therein from a heated air source attached by a fluid flow conduit to the inlet. The door further provides one or more outflow openings to permit escape of moisture laden heated air from the chamber. The door is adapted to fit in the opening of the autoclave provided for the conventional door thereof which is pivoted out of the way for use of the door in accordance with the invention.

In accordance with a yet further aspect of the invention, a supporting device is provided for support of medical or dental instruments off of the trays or other supporting surfaces within an autoclave. The instrument supporting device of the invention assists in drying by isolating instruments being sterilized from each other. The supporting device also provides the ability to position instruments at angles that enable drainage of liquids and attainment of more uniform temperatures throughout the instrument. The supporting device thus enhances sterilization in autoclaving and chemclaving. Supporting devices assist both in sterilization during steam autoclaving, chemclaving and during hot air drying in accordance with the present invention.

BRIEF DESCRIPTION OF DRAWINGS

The invention will be further set forth in the following detailed description and accompanying drawings wherein:

FIG. 1 is a perspective view of an autoclave of one type usable in connection with the invention, FIG. 2 is a rear perspective view of the autoclave of FIG. 1 with parts broken away to show the internal details thereof, FIG. 3 is a partially schematic view showing the arrangement of parts and control mechanisms used in connection with the invention, FIG. 4 is a front view of an autoclave showing a further embodiment of the invention and fitted with a venturi fluid flow outlet, FIG. 5 is a sectional view showing the venturi outlet of the device of FIG. 4, taken along Line 5—5, FIG. 6 is a fragmentary sectional view of a diffuser used in connection with a preferred embodiment for a fluid flow inlet into an autoclave of this invention, FIG. 7 is a partially schematic, fragmentary top sectional view of a device in accordance with a further embodiment of the invention, FIG. 7A is a sectional view of the fluid flow outlet of FIG. 7, FIG. 8 is a perspective view with parts in cross-section to show internal details in accordance with another embodiment of the invention, FIG. 9 is a sectional view of a cassette cover used in connection with the embodiment of FIG. 8, and FIG. 10 is a perspective view of an instrument-supporting device used in connection with the invention.

DETAILED DESCRIPTION OF THE DRAWINGS

As seen in FIGS. 1 and 2, an autoclave 10 of conventional design used for sterilization of medical and dental instruments under elevated heat and pressure includes an outer housing 12, an inner chamber 14 for containment of medical and dental instruments being sterilized and a door 16. Autoclaves 10 generally sterilize instruments by subjecting them to elevated temperatures of approximately 250°–300° Fahrenheit at pressures of 26–32 psi for approximately 5–25 minutes.

In accordance with the invention, a heating unit 20, preferably containing an internal fan 19 capable of blowing air at the rate of approximately 18–20 cubic feet per minute is attached to a conventional autoclave. The air is preferably heated by unit 20 so that it is about 160° F. to about 550° F. when it enters the autoclave chamber. The autoclave chamber 14 is penetrated in the rear either using an existing port or by forming an opening 22 therein. In some cases, for example, if it is essential to reduce electrical interference with electronic equipment, it has been found preferable not to use an internal fan 19, but rather to blow air through heating unit 20 by means of compressed air supplied to the heating unit from a remote compressor, instead.

Air heater/fan unit 19/20 is preferably installed under the outer housing 12 of autoclave unit 10. However, if desired, the unit may be positioned outside of the housing, for example above the top of the unit, if conditions dictate. The heater/fan unit is connected to an opening 22 in the autoclave chamber by means of a fluid flow pipe 24 preferably connected by means of a conduit coupling 26. Coupling 26 has one of its fluid flow pipes 27 connected to opening 22 as seen in FIG. 6. Solenoid valve 28 is provided to open and close the fluid flow path between heater unit 20 and autoclave chamber 14. Optionally, a vacuum pump 32 is connected to the fluid flow line between opening 22 and valve 28 or, as shown, to pipe 34 which is connected through a four-way coupling 33 to chamber 14 through a separate opening 35. Pressure relief valve 36 and steam trap 38 are conventional features on most autoclave systems.

In accordance with the alternate embodiment as seen in FIG. 3, a microswitch 37 is operated by a knob 39 actuated by closure of door 16. Switch 37 functions as a safety switch. When door 16 is closed thereby depressing knob 39, the start switch for heater 20 and fan 19 are disabled so that they cannot operate. This switch 37 also prevents solenoid 29 from opening valve 28. Thus, high pressure steam from the autoclave chamber 14 is prevented from flowing back into heater 20 and causing the electrical circuitry associated therewith from being shorted out.

When chamber door 16 is opened at the end of the pressure cycle, switch 37 is closed by extension of knob 39 thereby allowing the activation of solenoid 29 to open valve 28 and to start timer 21 causes heater 20 and fan 19 to be activated to begin moving heated air into chamber 14. At the end of the timed heated drying cycle, the heater element switch moves to the open position which allows fan 19 to blow unheated air into chamber 14. This causes sufficient cooling of instruments contained in chamber 14 so that they can be handled safely.

When vacuum pump 32 is included in the system, it can be activated prior to start up of fan 19 and heater 20 so that chamber 14 is evacuated of a portion of the moisture contained therein prior to start up of the drying cycle. In the case of some types of autoclaves, it has been found highly beneficial to remove some of the moisture and, thus, enabling faster drying.

As seen in FIG. 6, a diffuser plate 40 can be provided in opening 22 in order to cause turbulent flow of the heated air within chamber 14. It has been found that by staggering openings 42 in a plate 40 that spans opening 22 and providing alternate openings 44 that are provided with elongated nipples extending into conduit 27 that a cyclonic air flow pattern can be caused to occur within chamber 14. While the exact nature of the cause of the cyclonic flow is not fully understood, it is believed that the plate 40 having alternating nipples 44 and simple openings 42 cause pressure differentials to occur between various parts of the air stream flowing into chamber 14, thus, causing turbulent flow.

As best seen in FIGS. 4 and 5, the chamber 14, may optionally be provided with a venturi outlet 46 that includes a restricted air flow portion 48.

In the embodiment shown in FIGS. 4 and 5, a venturi outlet 46 provided with a portion of restricted cross-section 48 is used to draw moisture from within the autoclave. The venturi 46 creates a negative pressure by allowing air to enter through the larger diameter portion of the opening and then to be restricted to the smaller diameter portion wherein the flow velocity increases. The resultant vacuum has been found to draw moisture out of chamber 14 more rapidly. As seen in FIG. 4 venturi 46 can be pivotally attached to the front of housing 12. The venturi is placed in the position shown by phantom lines when autoclaving is taking place. During the drying process venturi 46 is pivoted so that it extends into the chamber 14, as shown. As seen in FIG. 5, door seal or gasket 49 closes tightly around the exterior of venturi 46 so that heated air from chamber 14 exits through the venturi.

Some autoclave units have chambers 14 which are difficult or dangerous to penetrate. In such cases, the drier unit 20 may be attached to autoclave chamber 14 by use of a door 60 which closes the opening to the autoclave when door 16 is in the open position. Drier/fan unit 19/20 is attached by conduit 27 directly to an opening 62 in door 60. Door 60 also contains an outflow opening 64 which permits flow of air out of chamber 14 when the drier unit is operating. The door gasket 66 provides for otherwise airtight closure of chamber 14. Outlet 64 may have a section of reduced diameter 65 thereby providing a venturi outlet in the embodiment of FIG. 7.

A still further embodiment of the invention is shown in FIGS. 8 and 9. In this alternate type of autoclave system, the instruments to be sterilized are positioned in a tray 70. Tray 70 is provided with an autoclaving cover (not shown) and with said cover in place is inserted into an autoclave unit wherein instruments contained in tray 70 are subjected to elevated heat and pressure.

In accordance with the present invention, the cover for tray 70 is removed. A separate unit 72 for receiving the cassette 70 for further drying is provided. Satellite unit 72 has an opening 73 for receipt of the tray 70 over which a cover 76 has been positioned for use during the heating step. Cover 76 is provided with an inflow opening connected to an elbow 75 which interfits with a conduit 74 by means of a quick coupling. Conduit 74 is connected to a fan/heater unit 19, 20 (not shown) which are of the same type previously discussed to deliver air heated to about 160° F. to 550° F. The air is heated to a temperature that assists with the drying process without causing thermal damage to the instruments.

Cover 76 may be provided with an internal baffle 78 causing the heated air to be uniformly dispersed throughout tray 70. At the sides of cover 76 are a plurality of openings 80 which direct the flow of heated air as indicated in FIG. 9. Each of the outer corners of cover 76 are located openings 82. Openings 82 may be formed by slight outward flaring of the corners of cover 76 or by cut out portions. The fan/heater assembly 19/20 used in conjunction with auxiliary heater device 72 is provided with a timer so that it functions in the same fashion as previously described relative to FIGS. 1-3.

Referring to FIG. 10, there is seen a device 90 for supporting a dental or medical instrument 89 during steam, chemclaving, and hot air drying procedures in accordance with the invention. Support device 90 includes opposite end support members 92 and 94 which are preferably in the form of an X-shaped frame. Ends 92 and 94 are connected at their lower ends by elongated intermediate members 96 which form a support base for supporting instrument 89 in a sterilization device spaced above the bottom floor thereof. Preferably, there are also upper elongated intermediate members 98 that connect the upper ends of frame members 92 with the opposite end members 94. Upper connecting members 98 form parallel lines which can, if desired, be used to support another similar supporting device 90 stacked on top of one another, preferably transversely to each other.

Support device 90 includes pairs 99, 101 and 100, 102 of resilient instrument engaging elements spaced along its length. In the preferred embodiment shown in FIG. 10, elements 99 and 101 adjacent end 92 of device 90 are biased toward each other to engage opposite sides of one end of instrument 89. At the opposite end of device 90 are members 100 and 102 which support the other end of instrument 89 in the same manner as elements 99 and 101. One of the pairs of instrument engaging elements is preferably of a greater height than the other so that the center line of the support created by elements 99 and 101 when holding instrument 89 are below the center line of support of elements 100 and 102. This allows the instrument 89 to be positioned in device 90 at an oblique angle relative to the base members 96, thus promoting drainage of moisture out of the instrument.

Elements 100 and 102 as well as elements 99 and 101 are affixed to transverse members 104 and 106, each of which is provided with bifurcated ends that engage to element 96 by snap on engagement thus allowing sliding movement along elements 96. The space between pairs of elements 99, 101 and 100, 102 is thus adjustable to accept different shapes and sizes of instruments 89 and to maintain a desired oblique angle relative to elements 96. The instrument is, thus, readily placed in element 90 by snapping it between elements 99 and 101, and 100 and 102.

Elements 99, 101 and 100, 102 are preferably formed from a resilient heat resistance plastic material such as a polyamide resin, butyl styrene polymer or a polycarbonate. The use of such materials isolates the instruments supported and thus minimizes electrolysis which may occur at the elevated temperatures used for sterilization. Frame components 92, 94, 96, 98 are formed of a rigid material such as stainless steel or a rigid plastic.

While preferred embodiments of the invention have been shown, it is to be understood that various modifications can be made by those skilled in the art that are equivalent to the preferred embodiment and, thus, are encompassed by the following claims.

What is claimed is:

1. A sterilization system comprising in combination an enclosed tray within which materials to be sterilized are subjected to a pressurized moist atmosphere at an elevated temperature, an auxiliary unit for causing a volume of air, heated to a temperature of about 160° F. to 550° F., to flow into said tray at a high air flow rate, said auxiliary unit being provided with an opening adapted to receive said tray, said tray being provided with first and second removable covers, said first cover being adapted to enclose said materials during sterilization, and said second cover being adapted to cover said tray for insertion into said auxiliary unit, said second cover having an air flow inlet interfitting with an air flow supply conduit in said auxiliary unit which conduit is connected to a source of heated air and said cover being provided with outflow openings for outflow of air.

2. A system according to claim 1 wherein an outflow opening is provided at each corner of said tray.

3. A system according to claim 2 wherein said cover includes a baffle for directing the flow of air from said inlet to each of the sides of said tray.

4. A system according to claim 2 wherein a fluid flow conduit with a quick connect coupling mating with a coupling on the inlet to said cover is provided for connecting said tray to said source of heated air.

* * * * *